(12) United States Patent
Nishiuchi et al.

(10) Patent No.: US 10,207,967 B2
(45) Date of Patent: Feb. 19, 2019

(54) METHOD AND APPARATUS FOR SEPARATING ALKYL AROMATIC HYDROCARBON

(71) Applicant: MITSUBISHI GAS CHEMICAL COMPANY, INC., Chiyoda-ku (JP)

(72) Inventors: Junya Nishiuchi, Kurashiki (JP); Shinichi Nagao, Kurashiki (JP); Yoshitaka Tanaka, Kurashiki (JP); Mitsuharu Kitamura, Kurashiki (JP); Hiroaki Oka, Kurashiki (JP)

(73) Assignee: MITSUBISHI GAS CHEMICAL COMPANY, INC., Chiyoda-ku (JP)

( * ) Notice: Subject to any disclaimer, the term of this patent is extended or adjusted under 35 U.S.C. 154(b) by 0 days.

(21) Appl. No.: 15/713,972

(22) Filed: Sep. 25, 2017

(65) Prior Publication Data

US 2018/0016209 A1   Jan. 18, 2018

Related U.S. Application Data

(62) Division of application No. 14/411,289, filed as application No. PCT/JP2013/067383 on Jun. 25, 2013, now Pat. No. 9,896,397.

(30) Foreign Application Priority Data

Jun. 29, 2012  (JP) .................................. 2012-147540

(51) Int. Cl.
  *C07C 7/10* (2006.01)
  *C07C 7/152* (2006.01)
  *B01D 11/04* (2006.01)

(52) U.S. Cl.
  CPC .............. *C07C 7/10* (2013.01); *B01D 11/043* (2013.01); *C07C 7/152* (2013.01)

(58) Field of Classification Search
  None
  See application file for complete search history.

(56) References Cited

U.S. PATENT DOCUMENTS 2,662,925 A   6/1951   McCaulay et al.
3,512,931 A   5/1970   Ueno et al.
(Continued)

FOREIGN PATENT DOCUMENTS

JP   41-006577 B1   4/1966
JP   47-019256 B    6/1972
(Continued)

OTHER PUBLICATIONS

International Search Report dated Oct. 1, 2013 in PCT/JP2013/067383 filed Jun. 25, 2013.
(Continued)

*Primary Examiner* — Tam M Nguyen
(74) *Attorney, Agent, or Firm* — Oblon, McClelland, Maier & Neustadt, L.L.P.

(57) ABSTRACT

A method for separating an alkyl aromatic hydrocarbon, the method having a step of adding a first diluent and an extractant having a superacid to a mixture comprising the alkyl aromatic hydrocarbon and one or more isomers thereof to carry out an acid-base extraction to thereby form a complex of the alkyl aromatic hydrocarbon with the superacid, and thereafter separating the complex from the mixture, and a step of adding an eliminating agent having a relative basicity in a range of 0.06 to 10 with respect to the alkyl aromatic hydrocarbon and a second diluent to the complex, and carrying out complex exchange of the alkyl aromatic hydrocarbon for the eliminating agent to thereby separate the alkyl aromatic hydrocarbon from the complex.

5 Claims, 1 Drawing Sheet

(56) References Cited

U.S. PATENT DOCUMENTS

| | | | |
|---|---|---|---|
| 3,592,865 A | 7/1971 | Long et al. | |
| 3,766,286 A | 10/1973 | Olah | |
| 5,177,302 A | 1/1993 | Uemasu et al. | |
| 2007/0155978 A1* | 7/2007 | Jungkamp | C07C 253/10 |
| | | | 558/322 |
| 2007/0249877 A1* | 10/2007 | McDonald | B01D 3/36 |
| | | | 570/178 |
| 2014/0194647 A1 | 7/2014 | Sainani | |
| 2015/0141730 A1 | 5/2015 | Nishiuchi et al. | |

FOREIGN PATENT DOCUMENTS

| | | |
|---|---|---|
| JP | 47-037408 B | 9/1972 |
| JP | 47-040782 B1 | 10/1972 |
| JP | 48-035041 B1 | 10/1973 |
| JP | 06-287149 A | 10/1994 |
| JP | 06-305989 A | 11/1994 |
| JP | 08-143485 A | 6/1996 |

OTHER PUBLICATIONS

D.A. McCaulay, et al., "Hyperconjugation in Aromatic Cation Complexes" Tetrahedron, vol. 5, 1959, pp. 186-193.
Office Action dated Dec. 5, 2016, in Taiwan Application No. 102123241.
Tamotsu Ueno "Japan gas-chemical xylene separation process", Bulletin of the Japan Petroleum Institute, 1970, 12, pp. 171-176.

* cited by examiner

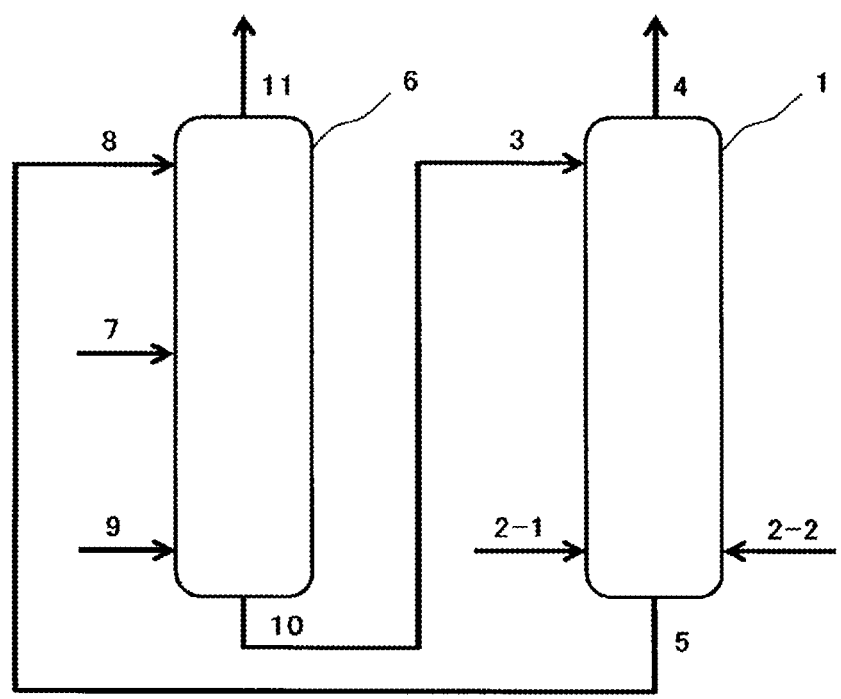

METHOD AND APPARATUS FOR SEPARATING ALKYL AROMATIC HYDROCARBON

CROSS-REFERENCE TO RELATED APPLICATIONS

The present application is a divisional application of U.S. patent application Ser. No. 14/411,289, which is a national stage of International Patent Application PCT/JP2013/067383, filed Jun. 25, 2013, which claims priority to Japanese Patent Application No. 2012-147540, filed Jun. 29, 2012. The contents of these applications are incorporated herein by reference in their entirety.

TECHNICAL FIELD

The present invention relates to a method for separating an alkyl aromatic hydrocarbon, particularly to a method for separating a specific alkyl aromatic hydrocarbon alone from a mixture of an alkyl aromatic hydrocarbon containing a plurality of isomers to thereby obtain a desired alkyl aromatic hydrocarbon in a high purity, and a separating apparatus of carrying out the method.

BACKGROUND ART

Polyalkyl aromatic hydrocarbons such as xylene and mesitylene have a plurality of isomers. For example, a mixed xylene obtained from petroleum-reformed oil or cracked gasoline contains 4 isomers of p-xylene, m-xylene, o-xylene and ethylbenzene. Since the plurality of isomers have boiling points close to one another, for example, p-xylene (hereinafter, abbreviated to "PX" in some cases) has a boiling point of 138° C.; m-xylene (hereinafter, abbreviated to "MX" in some cases) has a boiling point of 139° C.; and o-xylene (hereinafter, abbreviated to "OX" in some cases) has a boiling point of 144° C., it is difficult to obtain a desired compound from an isomer mixture by a usual distilling method of carrying out separation by utilizing the difference in boiling point.

Methods of separating a specific aromatic hydrocarbon alone from a mixture of aromatic hydrocarbons containing a plurality of isomers have been developed so far. For example, two types of methods of industrially separating MX from a mixed xylene are known. One method thereof is a known method of using an adsorbent having an affinity for MX, and adsorbing and separating MX alone from a mixed xylene, and for example, the method utilizes the principle of liquid chromatogram and adsorbs and separates MX, which has high affinity for an adsorbent such as zeolite, selectively from a mixed xylene to thereby obtain MX (see Patent Literature 1).

Another method is a method of using hydrogen fluoride and boron trifluoride being a superacid as an extractant, and the method of extracting and separating MX alone selectively from a mixed xylene by utilizing the fact that MX has a higher basicity than the other C8 aromatic hydrocarbon compounds (PX, OX and ethylbenzene). This method has an advantage of having a higher selectivity of MX than the above-mentioned method of using an adsorbent. For example, it is known that when MX is separated from a C8 aromatic hydrocarbon mixture, the selectivity of MX with respect to OX, which is a separation key component, is 2 in a method of using an adsorbent (see paragraph [0037] in Patent Literature 1), whereas the selectivity is 10 in the method of using hydrogen fluoride and boron trifluoride being a superacid and separating and extracting MX. Further, the method of using a superacid as an extractant allows extracting and separating mesitylene alone, which has a peculiarly high basicity, also from an isomer mixture of C9 alkyl aromatic hydrocarbons in addition to a mixed xylene because the difference, if any, in basicity among isomers in an isomer mixture can be utilized.

As a method of using hydrogen fluoride and boron trifluoride as an extractant and extracting and separating MX from a mixed xylene, Patent Literature 2 proposes a method in which a mixed xylene is fed from the central section of an extraction column; liquid hydrogen fluoride and boron trifluoride are fed from the column top section; a diluent is fed from the column bottom section; and countercurrent extraction is continuously carried out under the temperature condition of −20° C. to +30° C. to thereby extract a MX—HF—BF$_3$ complex into surplus hydrogen fluoride and separate MX from the mixed xylene.

Further, Patent Literature 3 proposes that a MX—HF—BF$_3$ complex is thermally decomposed in a decomposition column, and hydrogen fluoride and boron trifluoride are isolated and recycled. The Patent Literature describes that the complex is decomposed at a pressure of 2 to 10 atm and at a column bottom temperature of 131 to 217° C. while hexane as a decomposition auxiliary agent is evaporated and refluxed; and then, MX is withdrawn from the column bottom of the decomposition column, and hydrogen fluoride and boron trifluoride as the extractant are recovered from the column top and recycled.

It is further known that if a specific base is added to an aromatic hydrocarbon-HF—BF$_3$ complex such as a MX—HF—BF$_3$ complex, there occurs an equilibrium reaction of exchanging the complex states between the aromatic hydrocarbon and the base, and thus the utilization thereof enables measuring the relative basicities of individual aromatic hydrocarbons with respect to xylene (see Non Patent Literature 1). Non Patent Literature 1 describes a reaction shown below as a complex-forming reaction.

$$A+HF+BF_3 \rightarrow A \cdot H^+ + BF_4^-$$

In the above formula, "A" represents an aromatic hydrocarbon; and "A·H$^+$+BF$_4^-$" represents an aromatic hydrocarbon-HF—BF$_3$ complex.

CITATION LIST

Patent Literature

Patent Literature 1: Japanese Patent Laid-Open No. H8-143485
Patent Literature 2: Japanese Patent Publication No. S47-19256
Patent Literature 3: Japanese Patent Publication No. S47-37408

Non Patent Literature

Non Patent Literature 1: MaCaulay, D. A., and A. P. Lien, Tetrahedron, 1959, vol.5, pp.186-193

SUMMARY OF INVENTION

Technical Problem

In the extracting and separating method described in the above Patent Literature 2, the extraction column needs to be cooled at a low temperature of −20° C. to +30° C. so that the MX—HF—BF$_3$ complex is not deteriorated when the complex is formed. By contrast, when the decomposing auxiliary agent is added and hydrogen fluoride and boron trifluoride are isolated by thermal decomposition of the MX—HF—BF$_3$ complex, the column bottom of the decomposition column needs to be kept at a high temperature of 100° C. or more in order to thermally decompose the complex quickly while suppressing the deterioration of the complex because the MX—HF—BF$_3$ complex is deteriorated by heat. However, in consideration of the latent heat of hydrogen fluoride, the latent heat of the decomposing auxiliary agent, and the like, there arises a problem that a large amount of energy becomes necessary in order to maintain the column bottom at a high temperature.

Therefore, an object of the present invention is to provide a method in which an alkyl aromatic hydrocarbon is extracted and separated from a mixture containing the alkyl aromatic hydrocarbon and one or more isomers thereof by using a superacid such as hydrogen fluoride and boron trifluoride to thereby separate the desired alkyl aromatic hydrocarbon, and the method capable of largely reducing the energy necessary for the separation.

Further, another object of the present invention is to provide a separating apparatus to carry out the above separating method.

Solution to Problem

As a result of exhaustive studies to solve the above-mentioned problem, the present inventors have found that when a specific alkyl aromatic hydrocarbon is extracted and separated from the alkyl aromatic hydrocarbon containing a plurality of isomers such as a mixed xylene by using a specific superacid such as hydrogen fluoride and boron trifluoride, heating at the time of separating the alkyl aromatic hydrocarbon and the superacid can almost be eliminated by decomposing a complex of the alkyl aromatic hydrocarbon with the superacid by using a specific eliminating agent, and resultantly, the energy when the alkyl aromatic hydrocarbon such as MX is industrially separated can largely be reduced. It has been also found that the use of the specific eliminating agent enables a superacid (for example, hydrogen fluoride and boron trifluoride) to be recovered as a superacid solution of a complex of the eliminating agent with the superacid without isolating the superacid, and to be recycled again as an extractant as it is in the complex state. The present invention has been completed based on the finding.

That is, the present invention is as follows.

[1]

A method for separating an alkyl aromatic hydrocarbon comprising:

a step of adding a first diluent and an extractant comprising a superacid to a mixture comprising the alkyl aromatic hydrocarbon and one or more isomers thereof to carry out an acid-base extraction to thereby form a complex of the alkyl aromatic hydrocarbon with the superacid, and thereafter separating the complex from the mixture; and a step of adding an eliminating agent having a relative basicity in a range of 0.06 to 10 with respect to the alkyl aromatic hydrocarbon and a second diluent to the complex, and carrying out a complex exchange of the alkyl aromatic hydrocarbon for the eliminating agent to thereby separate the alkyl aromatic hydrocarbon from the complex.

[2]

The method for separating an alkyl aromatic hydrocarbon according to the above [1], further comprising a step of adding as the extractant a complex of the eliminating agent with the superacid formed by the complex exchange together with the second diluent to the mixture to thereby recycle the complex.

[3]

The method according to the above [1] or [2], comprising a step of adding an eliminating agent having the relative basicity in a range of 0.1 to 2.0 with respect to the alkyl aromatic hydrocarbon and the second diluent to the complex to carry out a complex exchange of the alkyl aromatic hydrocarbon for the eliminating agent to thereby separate the alkyl aromatic hydrocarbon from the complex.

[4]

The method according to any of the above [1] to [3], wherein the mixture comprising the alkyl aromatic hydrocarbon and one or more isomers thereof is C8 alkylbenzenes, C9 alkylbenzenes or C10 alkylbenzenes.

[5]

The method according to the above [4], wherein the mixture comprising the alkyl aromatic hydrocarbon and one or more isomers thereof is C8 alkylbenzenes, and the alkyl aromatic hydrocarbon is m-xylene.

[6]

The method according to any of the above [1] to [5], wherein the superacid is a mixed superacid of a Bronsted acid and a Lewis acid.

[7]

The method according to the above [6], wherein the complex of the eliminating agent with the superacid is added in such an amount that (the number of moles of the alkyl aromatic hydrocarbon in the mixture)/(the number of moles of the Lewis acid in the complex) is in a range of 0.5 to 1.5.

[8]

The method according to the above [6] or [7], wherein the first diluent is added in such an amount that (the volume of the first diluent)/(the number of moles of the Lewis acid in the superacid) is in a range of 50 mL/mol to 500 mL/mol.

[9]

The method according to any of the above [6] to [8], wherein the eliminating agent is added in an amount in a range of 1 to 15 in molar ratio with respect to the Lewis acid in the complex of the alkyl aromatic hydrocarbon with the superacid.

[10]

The method according to any of the above [1] to [9], wherein an amount of the second diluent with respect to the eliminating agent is in a range of 0.001 to 1 in terms of mass.

[11]

The method according to any of the above [1] to [10], wherein the eliminating agent has a boiling point of 145° C. to 400° C.

[12]

The method according to any of the above [6] to [11], wherein the Lewis acid is at least one selected from the group consisting of boron trifluoride, tantalum pentafluoride, niobium pentafluoride, titanium tetrafluoride, phosphorus pentafluoride, antimony pentafluoride and tungsten hexafluoride.

[13]

The method according to any of the above [6] to [12], wherein the Bronsted acid is hydrogen fluoride, and the Lewis acid is boron trifluoride.

[14]

The method according to any of the above [1] to [13], wherein the first and/or second diluent is an aliphatic saturated hydrocarbon and/or an alicyclic saturated hydrocarbon.

[15]
The method according to any of the above [1] to [14], wherein the first and/or second diluent is at least one selected from the group consisting of isohexane, 3-methylpentane, 2-methylhexane, 2-ethylhexane, decalin, tetrahydrodicyclopentadiene, ethylcyclohexane, methylcyclohexane and methylcyclopentane.

[16]
The method according to any of the above [6] to [15], wherein a proportion of the Brønsted acid with respect to the Lewis acid in the superacid is in a range of 5 to 20 in molar ratio.

[17]
An apparatus for separating an alkyl aromatic hydrocarbon comprising: an acid-base extraction column; and a complex exchange column,
wherein the acid-base extraction column comprises: a pipe for feeding a mixture comprising an alkyl aromatic hydrocarbon and one or more isomers thereof; a pipe for feeding a first diluent; a pipe for feeding a complex solution of an eliminating agent and a superacid withdrawn from a column bottom of the complex exchange column; a pipe for discharging the alkyl aromatic hydrocarbon as a complex solution of the alkyl aromatic hydrocarbon and the superacid from a column bottom of the acid-base extraction column; and a pipe for discharging a mixed liquid comprising the eliminating agent separated by the complex exchange, unextracted extraction residual isomers, and the diluent from a column top of the acid-base extraction column, and
wherein the complex exchange column comprises: a pipe for feeding the complex solution of the alkyl aromatic hydrocarbon and the superacid discharged from the column bottom of the acid-base extraction column; a pipe for feeding a second diluent and the eliminating agent; a pipe for discharging a mixed liquid comprising the extracted alkyl aromatic hydrocarbon, the eliminating agent and the diluent from a column top of the complex exchange column; and a pipe for discharging a complex solution of the eliminating agent and the superacid after the complex exchange has been carried out from the column bottom of the complex exchange column.

[18]
The apparatus according to the above [17], wherein the pipe for feeding the second diluent and the eliminating agent is separated into a pipe for feeding the second diluent and a pipe for feeding the eliminating agent.

[19]
The apparatus according to the above [17] or [18], wherein in the complex exchange column, the complex solution of the alkyl aromatic hydrocarbon and the superacid fed, and the fed mixed solution of the second diluent and the eliminating agent are brought into countercurrent contact.

[20]
The apparatus according to any of the above [17] to [19], further comprising a distillation column to distill the mixed liquid comprising the alkyl aromatic hydrocarbon, the eliminating agent and the diluent discharged from the complex exchange column to thereby separate the alkyl aromatic hydrocarbon, the eliminating agent and the diluent.

[21]
The apparatus according to any of the above [17] to [20], further comprising a distillation column to distill the mixed liquid comprising the eliminating agent, the unextracted extraction residual isomers and the diluent discharged from the acid-base extraction column to thereby separate the eliminating agent, the extraction residual isomers and the diluent.

Advantageous Effects of Invention

According to the present invention, in a method for extracting and separating an alkyl aromatic hydrocarbon from a mixture comprising the alkyl aromatic hydrocarbon and one or more isomers thereof, to thereby separate the desired alkyl aromatic hydrocarbon, the energy necessary for the separation can largely be reduced.

BRIEF DESCRIPTION OF DRAWING

The FIGURE illustrates a schematic view showing one embodiment of a separating apparatus to carry out the separating method according to the present invention.

DESCRIPTION OF EMBODIMENTS

Hereinafter, an embodiment (hereinafter, referred to as "the present embodiment") to carry out the present invention will be described in detail. The present invention is not limited to the following present embodiment, and may be carried out by making various changes and modifications within the gist. Here, in the drawing, the same symbols are assigned to the same elements, and duplicated description will be omitted. The positional relation including horizontal and vertical will be based on the positional relation shown in the drawing unless otherwise specified. The dimensional ratios of the apparatus and members are not limited to the ratios shown in the FIGURE.

<Method for Separating an Alkyl Aromatic Hydrocarbon>

A method for separating an alkyl aromatic hydrocarbon in the present embodiment comprises:
a step of adding a first diluent and an extractant comprising a superacid to a mixture comprising the alkyl aromatic hydrocarbon and one or more isomers thereof to carry out an acid-base extraction to thereby form a complex of the alkyl aromatic hydrocarbon with the superacid, and thereafter separating the complex from the mixture; and
a step of adding an eliminating agent having a relative basicity in a range of 0.06 to 10 with respect to the alkyl aromatic hydrocarbon and a second diluent to the complex to carry out complex exchange of the alkyl aromatic hydrocarbon for the eliminating agent to thereby separate the alkyl aromatic hydrocarbon from the complex.

The method for separating an alkyl aromatic hydrocarbon in the present embodiment involves selectively extracting and separating the alkyl aromatic hydrocarbon from a mixture comprising the alkyl aromatic hydrocarbon and one or more isomers thereof to thereby separate the specific alkyl aromatic hydrocarbon in a high purity. In order to separate a specific alkyl aromatic hydrocarbon in a high purity and efficiently from a mixture comprising two or more isomers of alkyl aromatic hydrocarbons having a difference in boiling point of 20° C. or less by a distilling operation, since high-degree superfractionation is necessary, the distilling operation is not practical from the industrial viewpoint including the production cost, the apparatus scale and the like. The separating method according to the present embodiment is especially suitable to separate a specific alkyl aromatic hydrocarbon from alkyl aromatic hydrocarbons comprising a plurality of such isomers having near boiling points.

The separating method according to the present embodiment involves adding a diluent and a superacid as an extractant to a mixture comprising an alkyl aromatic hydrocarbon and one or more isomers thereof to carry out acid-base extraction to thereby obtain an extract comprising a complex in a high purity of the alkyl aromatic hydrocarbon with the superacid from in the mixture. Thereafter, an eliminating agent whose relative basicity is in a specific range is added to the extract to carry out complex exchange to be thereby able to separate the alkyl aromatic hydrocarbon in a high purity from the extract. By returning the complex of the eliminating agent with the superacid formed by the complex exchange again to the mixture, since a complex of the alkyl aromatic hydrocarbon with the superacid is formed, the superacid can be recycled without isolating the superacid. Further, since the above method can recycle the complex of an eliminating agent with a superacid without being thermally decomposed, as an extractant, some heat quantity to isolate the superacid by decomposing the complex of an alkyl aromatic hydrocarbon with the superacid, as would be conventionally necessary, is unnecessary. As a result, the energy to separate an alkyl aromatic hydrocarbon can largely be reduced.

[Mixture Comprising an Alkyl Aromatic Hydrocarbon and One or More Isomers Thereof]

A mixture comprising an alkyl aromatic hydrocarbon and one or more isomers thereof used in the present embodiment is not especially limited, but from the viewpoint of the number of isomers having near boiling points, is preferably C8 alkylbenzenes, C9 alkylbenzenes or C10 alkylbenzenes. The C8 alkylbenzenes are a mixture comprising two or more selected from the group consisting of p-xylene (PX), m-xylene (MX), o-xylene (OX) and ethylbenzene; the C9 alkylbenzenes are a mixture comprising two or more selected from the group consisting of cumene, n-propylbenzene, ethyltoluene isomers (2-isomer, 3-isomer, 4-isomer) and trimethylbenzene isomers (1,2,4-isomer, 1,2,3-isomer); and the C10 alkylbenzenes are a mixture comprising two or more selected from the group consisting of isodurene (1,2,3,5-isomer) and other tetramethylbenzenes (1,2,4,5-isomer, 1,2,3,4-isomer) and dimethylethylbenzenes (1,3-dimethyl-5-ethyl-isomer, 1,4-dimethyl-2-ethyl-isomer, 1,3-dimethyl-4-ethyl-isomer, 1,2-dimethyl-4-ethyl-isomer, 1,3-dimethyl-2-ethyl-isomer, 1,2-dimethyl-3-ethyl-isomer). In the present embodiment, as a raw material, a mixture of isomers of the above-mentioned alkyl aromatic hydrocarbons is used, but the mixture may contain compounds other than the isomers, and the alkyl aromatic hydrocarbons are preferably contained in 90% or more in terms of mass with respect to the whole mixture.

The separating method according to the present embodiment involves selectively extracting and separating an alkyl aromatic hydrocarbon (hereinafter, also referred to as "specific alkyl aromatic hydrocarbon") having a highest basicity in a mixture from the mixture of alkyl aromatic hydrocarbons comprising isomers having small differences in boiling point as described above. A C8 alkylbenzene having a highest basicity in the above C8 alkyl aromatic hydrocarbons is MX; a C9 alkylbenzene having a highest basicity in the C9 alkyl aromatic hydrocarbons is mesitylene; and a C10 alkylbenzene having a highest basicity in the C10 alkyl aromatic hydrocarbons is isodurene. Therefore, in the method in the present embodiment, in the case of using C8 alkylbenzenes as a raw material, a substance to be extracted and separated is MX; in the case of using C9 alkylbenzenes as a raw material, a substance to be extracted and separated is mesitylene; and in the case of using C10 alkylbenzenes as a raw material, a substance to be extracted and separated is isodurene.

[Acid-Base Extracting Step]

The method for separating an alkyl aromatic hydrocarbon in the present embodiment comprises:

a step (acid-base extracting step) of adding a first diluent and an extractant comprising a superacid to a mixture comprising the alkyl aromatic hydrocarbon and one or more isomers thereof to carry out acid-base extraction to thereby form a complex of the alkyl aromatic hydrocarbon with the superacid, and thereafter separating the complex from the mixture.

(Superacid Used as an Extractant)

The separating method in the present embodiment involves first adding a superacid as an extractant to a mixture comprising the above specific alkyl aromatic hydrocarbon and at least one or more isomers thereof. Here, the "superacid" means an acid exhibiting a higher acid strength than 100% sulfuric acid, whose Hammett acidity function $H°$ is $-11.93$. The "superacid" includes not only an acid singly but further a solution of the acid. A superacid forms a complex with an alkyl aromatic hydrocarbon having a highest basicity in a mixture. A diluent is added to the mixture comprising the complex (hereinafter, also referred to as "alkyl aromatic hydrocarbon-superacid complex"), and components excluding the specific alkyl aromatic hydrocarbon in the mixture are stripped to be thereby able to extract the specific alkyl aromatic hydrocarbon in a complex state from the mixture.

A superacid used as an extractant is not especially limited, but examples thereof as Bronsted acids include fluorosulfuric acid ($FSO_3H$) and trifluoromethanesulfonic acid ($CF_3SO_3H$). A superacid may further be used which is of a mixed type in a combination of a Bronsted acid with a Lewis acid. Examples of the mixed type superacid include combinations of at least one or more selected from the group consisting of hydrogen fluoride (HF), hydrochloric acid (HCl), fluorosulfuric acid ($FSO_3H$), trifluoromethanesulfonic acid ($CF_3SO_3H$) and sulfuric acid ($H_2SO_4$) as Bronsted acids with at least one or more selected from the group consisting of antimony pentafluoride ($SbF_5$), boron trifluoride ($BF_3$), aluminum chloride ($AlCl_3$), tantalum pentafluoride ($TaF_5$), niobium pentafluoride ($NbF_5$), titanium tetrafluoride ($TiF_4$) and phosphorus pentafluoride ($PF_5$) as Lewis acids.

Among the above superacids, from the viewpoint of recycling of superacids, such a superacid is preferable that an alkyl aromatic hydrocarbon-superacid complex is present in a liquid state in the temperature range of $-50°$ C. to $+20°$ C. For example, use of a mixture of hydrogen fluoride with the above Lewis acid is preferable; more preferable are a mixture of hydrogen fluoride (HF) with boron trifluoride ($BF_3$), a mixture of hydrogen fluoride (HF) with tantalum pentafluoride ($TaF_5$), a mixture of hydrogen fluoride (HF) with niobium pentafluoride ($NbF_5$), a mixture of hydrogen fluoride (HF) with titanium tetrafluoride ($TiF_4$), a mixture of hydrogen fluoride (HF) with phosphorus pentafluoride ($PF_5$), a mixture of hydrogen fluoride (HF) with antimony pentafluoride ($SbF_5$), and a mixture of hydrogen fluoride (HF) with tungsten hexafluoride ($WF_6$); among these, a mixture of hydrogen fluoride (HF) with boron trifluoride ($BF_3$), which is a superacid having industrial utilization results, is especially preferable.

Here, the term "being present in a liquid state in the temperature range of $-50°$ C. to $+20°$ C." suffices if being present in a liquid state at any one temperature in the temperature range, and does not need to be present in a liquid state over the whole temperature range.

In the case of using the mixture of a Bronsted acid with a Lewis acid as a superacid, the mixture is preferably added in such amount that an alkyl aromatic hydrocarbon-superacid complex and an eliminating agent-superacid complex after a complex exchange reaction described later can maintain a complex state without releasing the Lewis acid (gas). Specifically, the molar ratio (the number of moles of a Bronsted acid/the number of moles of a Lewis acid) of the Bronsted acid to the Lewis acid in a superacid is preferably in the range of 5 to 50, and more preferably in the range of 5 to 20. If the molar ratio of a Bronsted acid to a Lewis acid in a superacid is in the above range, an alkyl aromatic hydrocarbon-superacid complex and/or an eliminating agent-superacid complex is likely to be able to be stably maintained while the volume efficiency of a reaction vessel to form the complex is maintained. Since the release as a gas of the Lewis acid from the superacid complex solution can effectively be suppressed, the amount of the alkyl aromatic hydrocarbon and the eliminating agent migrating into an oil phase containing the diluent and extraction residues is also likely to be able to be reduced. Further in the case of using hydrogen fluoride in the above proportion as a Bronsted acid, the eliminating agent-superacid complex can easily be controlled in a liquid state, which is therefore especially preferable.

(First Diluent Used in the Acid-Base Extracting Step)

In the present description, a diluent used in the acid-base extracting step is called "a first diluent", and a diluent used in the complex exchanging step is called "a second diluent". Here, the case of being called simply "a diluent" indicates each diluent singly, or indicates a mixture of the first diluent with the second diluent.

The first diluent to be added in the acid-base extracting step is preferably added in an amount enough to strip components excluding a complex in the components extracted with an extractant, that is, alkyl aromatic hydrocarbons excluding a specific alkyl aromatic hydrocarbon physically dissolved by the complex. As described later, in the case of recycling an eliminating agent-superacid complex, the first diluent is preferably added in an amount enough to complex-exchange the eliminating agent-superacid complex to thereby make a specific alkyl aromatic hydrocarbon-superacid complex.

The first diluent usable is not especially limited as long as dissolving alkyl aromatic hydrocarbons, but from the viewpoint of suppressing side-reactions such as disproportionation reaction and polymerization caused by an alkyl aromatic hydrocarbon in the presence of a superacid, use of an aliphatic or alicyclic saturated hydrocarbon is preferable. Examples of the aliphatic or alicyclic saturated hydrocarbon include n-hexane, n-heptane, n-decane, isohexane, 3-methylpentane, 2-methylhexane, 2-ethylhexane, cis-decalin, tetrahydrodicyclopentadiene, ethylcyclohexane, methylcyclohexane, methylcyclopentane, cis-1,2-dimethylcyclohexane, 1,3-dimethyladamantane and decahydroacenaphthene, and these can be used singly or as a mixture of two or more.

In addition to the above saturated hydrocarbon, other saturated hydrocarbons comprising no quaternary carbon atom may be used concurrently, but in this case, the volume efficiency of an apparatus is decreased in some cases. Further, the first diluent preferably contains no impurities having unsaturated bonds and no impurities comprising atoms other than carbon and hydrogen.

Among the above saturated hydrocarbons, from the viewpoint of suppressing the disproportionation reaction, more preferable are isohexane, 3-methylpentane, 2-methylhexane, 2-ethylhexane, cis-decalin, tetrahydrodicyclopentadiene, ethylcyclohexane, methylcyclohexane, methylcyclopentane, cis-1,2-dimethylcyclohexane, 1,3-dimethyladamantane and decahydroacenaphthene; and especially preferable are methylcyclopentane, cis-decalin, decahydroacenaphthene, cis-1,2-dimethylcyclohexane, 1,3-dimethyladamantane and decahydroacenaphthene.

[Complex Exchanging Step]

The method for separating an alkyl aromatic hydrocarbon in the present embodiment comprises:

a step (complex exchanging step) of adding an eliminating agent having a relative basicity in the range of 0.06 to 10 with respect to the alkyl aromatic hydrocarbon and a second diluent to the complex to complex-exchange the alkyl aromatic hydrocarbon by the eliminating agent to thereby separate the alkyl aromatic hydrocarbon from the complex.

(Eliminating Agent)

By adding a specific eliminating agent to an alkyl aromatic hydrocarbon-superacid complex as which the alkyl aromatic hydrocarbon has been extracted and separated in the acid-base extracting step, exchange of the complex states (complex exchange) is carried out to thereby separate the desired alkyl aromatic hydrocarbon. That is, an alkyl aromatic hydrocarbon-superacid complex and an eliminating agent-superacid complex after the complex exchange hold the following equilibrium reaction.

Formula 1

$$A_1H^+ + A_2 \leftrightarrow A_1 + A_2H^+ \qquad (I)$$

In the formula, $A_1$ is an alkyl aromatic hydrocarbon; $A_1H^+$ is an alkyl aromatic hydrocarbon-superacid complex; $A_2$ is an eliminating agent; and $A_2H^+$ is an eliminating agent-superacid complex.

In the present embodiment, the basicity of an alkyl aromatic hydrocarbon being a target compound to be extracted is paid attention to, and it has been found that by adding an eliminating agent having a relative basicity in the range of 0.06 to 10 with respect to the alkyl aromatic hydrocarbon, the high-purity and desired alkyl aromatic hydrocarbon can be separated into an oil phase, and as described later, the superacid can be recycled without being isolated. Here, in the present embodiment, the "relative basicity" of an eliminating agent ($A_2$) with respect to an alkyl aromatic hydrocarbon ($A_1$) is defined as a value calculated from the following expression at a liquid temperature of 0° C.

Relative basicity=(the number of moles of $A_2H^+$/the number of moles of $A_2$)/(the number of moles of $A_1H^+$/the number of moles of $A_1$)

A calculating method of a relative basicity of an eliminating agent will be described taking as an example the case of using MX as an alkyl aromatic hydrocarbon and HF—BF$_3$ as a superacid. Anhydrous hydrogen fluoride, MX, hexane and an eliminating agent are charged in a molar ratio of 4.0:0.32:0.95:0.66 in a temperature-controllable autoclave (SUS316L-made) having an internal volume of 500 mL and equipped with an electromagnetic stirrer, and the content is stirred and held at a liquid temperature of −10° C. Then, boron trifluoride as a Lewis acid in a molar proportion (the number of moles of boron trifluoride/the number of moles of hydrogen fluoride) of 0.1 with respect to anhydrous hydrogen fluoride is fed to the reactor at a rate of 2 L/min, and held at 0° C. for 30 min. Thereafter, the stirring is suspended for 10 min to make the resultant stand still; a hydrogen fluoride solution phase and an oil phase thus separated into the two phases are each collected in ice water; and the obtained oil phase is neutralized and washed with water, and then analyzed by gas chromatography. By substituting the number of moles (the components present in the hydrogen fluoride solution phase are regarded as HF-Lewis acid complexes) of MX and the eliminating agent in the hydrogen fluoride solution phase and the oil phase each acquired by the analysis result into the above calculation expression, the relative basicity at a liquid temperature of 0° C. with respect to MX can be calculated.

The use of an eliminating agent having a relative basicity in the above range with respect to an alkyl aromatic hydrocarbon (for example, MX) to be separated makes the exchange of complex states between an alkyl aromatic hydrocarbon-superacid complex and the eliminating agent, and between the alkyl aromatic hydrocarbon and the eliminating agent-superacid complex to easily progress. If the relative basicity is less than 0.06, although the acid-base extraction becomes easy, the complex exchange reaction between the alkyl aromatic hydrocarbon-superacid complex and the eliminating agent hardly progresses and a large amount of the eliminating agent becomes necessary. Hence, in the industrial operation, a decrease of the volume efficiency of a reaction vessel in which the complex exchange by an eliminating agent is carried out is brought about. By contrast, if the relative basicity exceeds 10, although the complex exchange reaction between the alkyl aromatic hydrocarbon-superacid complex and the eliminating agent easily progresses, when the eliminating agent-superacid complex obtained by the complex exchange is recycled, the complex exchange reaction between the alkyl aromatic hydrocarbon and the eliminating agent-superacid complex hardly progresses, and a large amount of a raw material mixture becomes necessary. Hence, in the industrial operation, the volume efficiency of a reaction vessel in which the alkyl aromatic hydrocarbon-superacid complex is formed is decreased, and decreases in the economic efficiency and the production efficiency are brought about.

In the separating method in the present embodiment, use of an eliminating agent is preferable which has a relative basicity with respect to an alkyl aromatic hydrocarbon in the range of 0.08 to 6.0, more preferable which has a relative basicity in the range of 0.10 to 4.0, still more preferable which has a relative basicity of 0.10 to 2.0, and especially preferable which has a relative basicity of 0.15 to 2.0. Such eliminating agents to be suitably used are aromatic hydrocarbons, but among these, aromatic hydrocarbons capable of stably forming an eliminating agent-superacid complex are more preferably used. Further from the viewpoint of the extractant being recycled, the eliminating agent as a single substance and the eliminating agent-superacid complex are preferably in a liquid state in the range of −50 to +20° C. In the case of using an HF-Lewis acid as a superacid, an eliminating agent-superacid complex can easily be controlled in a liquid state by adjusting the proportion of hydrogen fluoride, which is therefore especially preferable.

For example, the above Non Patent Literature 1 omits the detailed measuring method, but describes the relative basicities of alkyl aromatic hydrocarbons in the case where the relative basicity of p-xylene (PX) is taken to be 1. According to this literature, the relative basicities of C8 to C9 alkyl aromatic hydrocarbons are as shown in the following Table 1; and an eliminating agent may suitably be selected by reference to these data.

TABLE 1

| Alkyl Aromatic Hydrocarbon | | Relative Basicity |
|---|---|---|
| C8 | PX | 1 |
| | OX | 2 |
| | MX | 20 |
| C9 | pseudocumene | 40 |
| | hemimellitene | 40 |
| | mesitylene | 2800 |
| C10 | durene | 120 |
| | 1,2,3,4-tetramethylbenzene | 170 |
| | isodurene | 5600 |

As the eliminating agent, from the viewpoint of being capable of more easily separating a specific alkyl aromatic hydrocarbon by a distilling operation, an aromatic hydrocarbon is preferably used which has a higher boiling point than that of the specific alkyl aromatic hydrocarbon to be separated; and an aromatic hydrocarbon is more preferably used which has a boiling point in the range of 145 to 400° C. For example, in the case where MX is made to be a target compound as an alkyl aromatic hydrocarbon to be separated, eliminating agents suitably usable are 3-ethyltoluene, 1-methyl-3-propylbenzene, metadiethylbenzene, 1-fluoronaphthalene, 1,3,5-triethylbenzene, 3-methylbiphenyl, fluoro-2,4,6-trimethylbenzene, fluoro-2,3,6-trimethylbenzene, fluoro-3,4,5-trimethylbenzene, fluoro-2,3,5-trimethylbenzene, 1,3-dimethyl-4-(2,2-dimethylpropyl)benzene, 1,3-dimethyl-5-(2,2-dimethylpropyl)benzene, 1-methyl-3,5-di (2,2-dimethylpropyl)benzene, 1-isobutyl-3-methylbenzene, and the like; and these eliminating agents can be used singly or as a mixture of two or more.

Particularly in the case where C8 alkylbenzenes as alkyl aromatic hydrocarbons are used and MX is extracted as a specific alkyl aromatic hydrocarbon from a mixture thereof, as the eliminating agent, 3-ethyltoluene, metadiethylbenzene or a mixture thereof can suitably be used. Further in the case where C9 alkylbenzenes as alkyl aromatic hydrocarbons are used and mesitylene is extracted as a specific alkyl aromatic hydrocarbon from a mixture thereof, as the eliminating agent, 1,3,5-triethylbenzene or the like can suitably be used.

The amount of an eliminating agent added is not especially limited as long as being an amount capable of carrying out complex exchange of an alkyl aromatic hydrocarbon-superacid complex, but is suitably determined according to the amount of the specific alkyl aromatic hydrocarbon-superacid complex, the relative basicity of the eliminating agent and the capability of the reaction vessel to carry out the complex exchange in. In order to industrially produce a specific alkyl aromatic hydrocarbon, the amount of an eliminating agent added is preferably an amount of being capable of carrying out complex exchange in the number of theoretical plates of a reaction vessel to carry out the complex exchange in being in the range of 5 plates to 10 plates. From the above viewpoint, in the present embodiment, in the case of using a mixture of a Bronsted acid with a Lewis acid as a superacid, an eliminating agent is added preferably in such an amount as to become in the range of 1 to 15 in molar ratio with respect to the Lewis acid in a complex of an alkyl aromatic hydrocarbon with the superacid. By making the amount of an eliminating agent added to be in the above range, since the complex exchange reaction of an alkyl aromatic hydrocarbon-Bronsted acid-Lewis acid complex with the eliminating agent easily progresses, the number of theoretical plates of a reaction vessel can be reduced and the concentration of an alkyl aromatic hydrocarbon to be extracted is raised, thereby being likely to be capable of improving the distilling efficiency. In consideration of the scale and the volume efficiency of a reaction vessel, the amount is more preferably such an amount as to become in the range of 1.1 to 10 in molar ratio with respect to the Lewis acid in a complex of an alkyl aromatic hydrocarbon with the superacid.

(Second Diluent Used in the Complex Exchanging Step)

In the complex exchanging step, by adding a second diluent together with an eliminating agent, the alkyl aromatic hydrocarbon separated by the complex exchange is extracted and separated as a mixed solution with the eliminating agent and the second diluent, and the alkyl aromatic hydrocarbon alone can further be obtained by well-known means such as distillation. Therefore, the second diluent is added preferably in such an amount as to be able to separate a superacid solution and an oil phase (a mixed solution of the alkyl aromatic hydrocarbon, the eliminating agent and the second diluent). The addition of the second diluent enables to suppress the disproportionation reaction of the eliminating agent in the complex exchange reaction. The amount of the second diluent added capable of separating the superacid solution and the oil phase and suppressing the disproportionation reaction of the eliminating agent as described above is preferably in the range of 0.001 to 1 in mass ratio (the mass of the second diluent/the mass of the eliminating agent) with respect to the eliminating agent to be added, and more preferably in the range of 0.01 to 0.25. Making the amount of the second diluent added to be in the above range is advantageous for the separation of the superacid solution and the oil phase and the suppression of the disproportionation reaction of the eliminating agent, and advantageous also from the viewpoint of the economic efficiency and the production efficiency.

Second diluents usable are the same as the first diluents described above.

<Recycling of the Superacid>

The separating method according to the present embodiment preferably further comprises a step of adding, as an extractant, the complex of the eliminating agent with the superacid formed by the complex exchange together with the second diluent to the mixture comprising the alkyl aromatic hydrocarbon and one or more isomers thereof to thereby recycle the superacid. The eliminating agent-superacid complex formed by the complex exchange is continuously added to the original mixture and recycled without the superacid (for example, hydrogen fluoride and a Lewis acid) being isolated. In the case of comprising the above step, since there is no need for the isolating operation of a superacid, which would be necessary conventionally, the energy necessary for the separation of an alkyl aromatic hydrocarbon can largely be reduced. Here, in the eliminating agent-superacid complex to be added to the original mixture, the alkyl aromatic hydrocarbon-superacid complex which has not been completely complex-exchanged in the complex exchanging step may be partially contained. Further, when the eliminating agent-superacid complex is added to the original mixture and again subjected to the acid-base extracting step, in the alkyl aromatic hydrocarbon-superacid complex discharged after the acid-base extracting step, the eliminating agent-superacid complex which has not been completely complex-exchanged by the alkyl aromatic hydrocarbon, which is carried out simultaneously with the acid-base extraction, may be partially contained.

The eliminating agent-superacid complex is added to the mixture comprising the alkyl aromatic hydrocarbon and isomers thereof, and the complex exchange is thereby again carried out and the alkyl aromatic hydrocarbon is acid-base-extracted as a complex with the superacid. Therefore, the first diluent to be added to a reaction vessel to carry out the complex formation therein is added preferably in an amount of being capable of stripping the other alkyl aromatic hydrocarbons (that is, the isomers), which are physically dissolved in a superacid solution of the alkyl aromatic hydrocarbon-superacid complex and do not form complexes.

(First Diluent in an Acid-Base Extraction Column in Superacid Recycling)

Describing the case of using as a superacid a mixture of a Bronsted acid with a Lewis acid as an example, the amount (the volume of the diluent (mL)/the number of moles of the Lewis acid in a superacid solution) of a first diluent with respect to the amount of the Lewis acid in the superacid solution is preferably in the range of 50 mL/mol to 500 mL/mol, and more preferably in the range of 100 mL/mol to 300 mL/mol. Since making the amount of the first diluent added to be in the above range enables to sufficiently carry out stripping while maintaining the volume efficiency of a reaction vessel, and enables to make high the content of an alkyl aromatic hydrocarbon-Bronsted acid-Lewis acid complex extracted as a hydrogen fluoride solution, a high-purity alkyl aromatic hydrocarbon is likely to be able to be obtained even if the number of theoretical plates of the reaction vessel is small.

As described above, the superacid solution comprising the eliminating agent-superacid complex is added to the mixture comprising the alkyl aromatic hydrocarbon and isomers thereof; thereby, the complex exchange is again carried out, and since the superacid solution comprising the eliminating agent-superacid complex functions as an extractant, the alkyl aromatic hydrocarbon in the mixture is extracted as an alkyl aromatic hydrocarbon-superacid complex by the acid-base extraction. For example, in the case of using a mixture of a Bronsted acid with a Lewis acid as the superacid, in order for the complex exchange and the acid-base extraction to be carried out, the superacid solution comprising the eliminating agent-superacid complex is added, as an extractant, in such an amount that the number of moles of the alkyl aromatic hydrocarbon in the mixture/the number of moles of the Lewis acid in the complex becomes in the range of 0.5 to 1.5, to the mixture. By adjusting the amounts of the mixture and the eliminating agent-superacid complex to be in the above ranges, the complex exchange reaction of the eliminating agent-superacid complex with the alkyl aromatic hydrocarbon is likely to easily progress. The resultant discharge as an oil phase of the alkyl aromatic hydrocarbon not having been complex-exchanged together with the other isomers being extraction residual components, the diluent and the eliminating agent is likely to be able to be reduced.

<Apparatus for Separating an Alkyl Aromatic Hydrocarbon>

Then, an apparatus for separating an alkyl aromatic hydrocarbon in the present embodiment will be described by reference to the Figure.

An apparatus for separating an alkyl aromatic hydrocarbon in the present embodiment is a separating apparatus comprising an acid-base extraction column and a complex exchange column, wherein the acid-base extraction column comprises a pipe for feeding a mixture comprising an alkyl aromatic hydrocarbon and one or more isomers thereof, a pipe for feeding a first diluent, a pipe for feeding a complex solution of an eliminating agent and a superacid withdrawn from the column bottom of the complex exchange column, a pipe for discharging the alkyl aromatic hydrocarbon as a complex solution of the alkyl aromatic hydrocarbon and the superacid from the column bottom of the acid-base extraction column, and a pipe for discharging a mixed liquid comprising the eliminating agent separated by the complex exchange, unextracted extraction residual isomers, and the diluent from the column top of the acid-base extraction column, and wherein the complex exchange column comprises a pipe for feeding the complex solution of the alkyl aromatic hydrocarbon and the superacid discharged from the column bottom of the acid-base extraction column, a pipe for feeding a second diluent and an eliminating agent, a pipe for discharging a mixed liquid comprising the extracted alkyl aromatic hydrocarbon, the eliminating agent and the diluent from the column top of the complex exchange column, and a pipe for discharging a complex solution of the eliminating agent and the superacid after the complex exchange has been carried out from the column bottom of the complex exchange column.

The FIGURE illustrates a schematic view showing one embodiment of a refining apparatus to carry out the refining method according to the present invention. The FIGURE is an example having a pipe 5 to carry out a step of adding as an extractant a complex of an eliminating agent and a superacid together with a second diluent to a mixture, and recycling the complex. Although the FIGURE is an example in which the second diluent is fed through a pipe 2-1 to a lower part of the complex exchange column; the eliminating agent is fed through a pipe 2-2 to a lower part thereof; and the both are mixed in the column lower section; that is, pipes for feeding the second diluent and the eliminating agent are separated, the second diluent and the eliminating agent may be previously mixed, and fed through one pipe. Hereinafter, an example will be described in which MX, which has a highest basicity among a mixed xylene, is extracted and separated using a superacid from the mixed xylene being alkyl aromatic hydrocarbons to thereby refine MX.

First, a mixed xylene being a raw material is fed through a pipe 7 to an acid-base extraction column 6 to extract MX in the mixed xylene as a MX-superacid complex. A first diluent is fed through a pipe 9 arranged at a lower part of the acid-base extraction column to the acid-base extraction column 6. A superacid solution of an eliminating agent-superacid complex withdrawn from the column bottom 5 of a complex exchange column 1 to carry out a complex exchange reaction to complex-exchange the MX-superacid complex by an eliminating agent is fed through a pipe 8 to an upper part of the acid-base extraction column 6. In the acid-base extraction column 6, a complex exchange of the eliminating agent-superacid complex by MX is carried out; MX is acid-base-extracted as the MX-superacid complex; and a superacid solution of the MX-superacid complex is continuously withdrawn from the column bottom 10 of the acid-base extraction column 6. The eliminating agent separated by the complex exchange, unextracted extraction residual xylene and the diluent are continuously withdrawn as a mixed liquid from the column top 11 of the acid-base extraction column 6. In the case of using as a superacid a mixture of a Bronsted acid with a Lewis acid, the superacid solution of the eliminating agent-superacid complex can be called also a Bronsted acid solution of an eliminating agent-Bronsted acid-Lewis acid-complex; and the superacid solution of the MX-superacid complex can be called also a Bronsted acid solution of a MX-Bronsted acid-Lewis acid-complex.

The superacid solution of the MX-superacid complex withdrawn from the acid-base extraction column 6 is fed through a pipe 3 to an upper part of the complex exchange column 1. The second diluent is fed through the pipe 2-1 to a lower part of the complex exchange column; and the eliminating agent is fed through the pipe 2-2 to a lower part thereof; and the both are mixed in the column lower section. In the complex exchange column 1, the MX-superacid complex solution, and the mixed solution of the second diluent and the eliminating agent are brought into countercurrent contact. The complex exchange is carried out herein to thereby separate the MX-superacid complex into MX and the eliminating agent-superacid complex. The separated MX is continuously withdrawn as a mixed liquid of the surplus eliminating agent and the diluent from the column top 4 of the complex exchange column 1. The complex-exchanged eliminating agent-superacid complex is, as described above, continuously withdrawn as the superacid solution from the column bottom 5 of the complex exchange column 1, and again fed through the pipe 5 to the acid-base extraction column 6 and thus recycled.

The separating apparatus in the present embodiment preferably further comprises a distillation column in which the mixed liquid comprising the alkyl aromatic hydrocarbon, the eliminating agent and the diluent discharged from the complex exchange column is distilled and separated into the alkyl aromatic hydrocarbon, the eliminating agent and the diluent. In this case, the mixed liquid comprising the eliminating agent, the unextracted extraction residual xylene and the diluent discharged from the column top 11 of the acid-base extraction column 6 is separated through a well-known distillation column (not shown in the FIGURE) into extraction residual xylene, the eliminating agent and the diluent.

The separating apparatus in the present embodiment preferably further comprises a distillation column in which the mixed liquid comprising the eliminating agent, the unextracted extraction residual isomers and the diluent discharged from the acid-base extraction column is distilled and separated into the eliminating agent, the extraction residual isomers and the diluent. In this case, the mixed liquid comprising MX, the eliminating agent and the diluent discharged from the column top 4 of the complex exchange column 1 is separated through a well-known distillation column (not show in the FIGURE) into MX, the eliminating agent and the diluent. A high-purity MX can thus be separated from the mixed xylene.

As the complex exchange column 1 and the acid-base extraction column 6, well-known means applied to liquid-liquid extracting operation systems can be used without especial limitation, and a packed column, a perforated plate column, a perforated plate pulse column, a stirrer-equipped acid-base extraction column, a WINTRAY (R), a mixer settler, and the like can suitably be used. Among these, types exhibiting a high treatment amount per unit cross-sectional area and a high extraction efficiency can be used preferably.

In the case where a superacid is add to a mixture, not limited to a mixed xylene, comprising an alkyl aromatic hydrocarbon and isomers thereof, if the temperature is high, the disproportionation reaction and the polymerization reaction vigorously occur. Further, since the superacid is used as an extractant, if the temperature is high, corrosion of the complex exchange column 1 and the acid-base extraction column 6 advances. Hence, the internal temperature of the complex exchange column 1 and the acid-base extraction column 6 is held preferably in the temperature range of −50° C. to +20° C., and more preferably in the temperature range of −30° C. to 0° C. If the internal temperature of the complex exchange column 1 and the acid-base extraction column 6 is in the above temperature range, the deterioration of the complex is likely to be able to be reduced. From the above viewpoint, although it can be said to be preferable that they are held at a temperature as low as possible, excessive cooling exhibits a disadvantage of bringing about a rise in the separation cost.

In the case of using HF—$BF_3$ as a superacid, the internal pressure of the complex exchange column 1 and the acid-base extraction column 6 is higher than thereof the vapor pressure of the MX—HF—$BF_3$ complex and the eliminating agent-HF—$BF_3$ complex, and can suitably be selected as a pressure exhibiting no trouble on the operation of the column. Specifically, the internal pressure of the complex exchange column 1 and the acid-base extraction column 6 is preferably in the pressure range of 0.2 MPa to 10 MPa, and more preferably in the pressure range of 0.25 MPa to 1 MPa. If the internal pressure is made too low, boron trifluoride (gas) is released from the HF—$BF_3$ complex, and the complex state is not maintained in some cases. By contrast, if the internal pressure is too high, since a column having a material and structure withstanding the pressure needs to be prepared, a rise in the separation cost is likely to be brought about.

EXAMPLES

Hereinafter, the present invention will be described in more detail by way of Examples, but the present invention is not especially limited to the following Examples.
<Measurement of the Relative Basicity>
Sample 1

50 g of anhydrous hydrogen fluoride (2.5 mol, made by MORITA CHEMICAL INDUSTRIES CO., LTD.) was charged in a temperature-controllable autoclave (SUS316L-made) having an internal volume of 500 mL and equipped with an electromagnetic stirrer, and the content was stirred and held at a liquid temperature of −10° C. Then, 122.9 g (MX: 0.20 mol, 3-ethyltoluene: 0.41 mol, n-hexane: 0.59 mol) of a raw material liquid obtained by mixing MX (made by MITSUBISHI GAS CHEMICAL COMPANY, INC.), 3-ethyltoluene (reagent grade, made by Tokyo Chemical Industry Co., Ltd.), and n-hexane (reagent grade, made by Wako Pure Chemical Industries, Ltd.) in a molar ratio of 1:2:3 was fed at a rate of 4 g/min to the reactor. Then, the liquid temperature in the reactor was cooled to −10° C.; thereafter, 17.0 g (0.25 mol) of boron trifluoride (made by STELLACHEMIFA CORPORATION) was fed at a rate of 6 g/min to the reactor, and the liquid was heated to 0° C., and held for 30 min. Thereafter, the stirring was suspended and the reaction liquid was allowed to stand still for 10 min; then, it was confirmed that the reaction liquid was separated into a hydrogen fluoride solution phase and an oil phase. The separated hydrogen fluoride solution phase and oil phase were each withdrawn into ice water. The obtained hydrogen fluoride solution phase and oil phase were each subjected to a neutralization treatment to thereby obtain an oil fraction dissolved in the hydrogen fluoride solution and an oil fraction obtained by removing trace amounts of acid fractions from the oil phase, respectively. The relative basicity of 3-ethyltoluene was determined from the reaction result acquired by gas chromatography, and was 0.52. Here, the analysis involved using gas chromatography (GC-14B, made by SHIMADZU CORPORATION) and fabricating a calibration curve using n-decane (reagent grade, made by Wako Pure Chemical Industries, Ltd.) as the internal standard substance for the evaluation. A capillary column used was ULBON Xylene Master, made by SHINWA CHEMICAL INDUSTRIES LTD. (internal diameter: 0.32 mmφ, length: 50 m). The temperature-rise program was such that the temperature was raised at a rate of 2° C./rain from 70° C. to 150° C., and held for 30 min.
Sample 2

The relative basicity was measured as in Sample 1, except for using 1-fluoronaphthalene (reagent grade, made by Tokyo Chemical Industry Co., Ltd.) in place of 3-ethyltoluene. The relative basicity of 1-fluoronaphthalene was 0.37.
Sample 3

The relative basicity was measured as in Sample 1, except for using fluoro-2,3,4,6-tetramethylbenzene (made by Shin Nippon Yakugyo Co., Ltd.) in place of 3-ethyltoluene. The relative basicity of 1-fluoro-2,3,4,6-tetramethylbenzene was 0.29.
Sample 4

The relative basicity was measured as in Sample 1, except for using metadiethylbenzene (reagent grade, made by Tokyo Chemical Industry Co., Ltd.) in place of 3-ethyltoluene. The relative basicity of metadiethylbenzene was 0.28.
Sample 5

The relative basicity was measured as in Sample 1, except for using fluoro-2,4,6-trimethylbenzene (reagent grade, made by Tokyo Chemical Industry Co., Ltd.) in place of 3-ethyltoluene. The relative basicity of fluoro-2,4,6-trimethylbenzene was 0.16.
Sample 6

The relative basicity was measured as in Sample 1, except for using pseudocumene (reagent grade, made by Wako Pure Chemical Industries, Ltd.) in place of 3-ethyltoluene. The relative basicity of pseudocumene was 1.63.
Sample 7

The relative basicity was measured as in Sample 1, except for using mesitylene (reagent grade, made by Wako Pure Chemical Industries, Ltd.) in place of 3-ethyltoluene. The relative basicity of mesitylene was 5.00.
Sample 8

The relative basicity was measured as in Sample 1, except for using OX (reagent grade, made by Wako Pure Chemical Industries, Ltd.) in place of 3-ethyltoluene. The relative basicity of OX was 0.04.
Sample 9

The relative basicity was measured as in Sample 1, except for using 1,3,5-triethylbenzene (reagent grade, made by Tokyo Chemical Industry Co., Ltd.) in place of 3-ethyltoluene. The relative basicity of 1,3,5-triethylbenzene was 3.52.
Sample 10

The relative basicity was measured as in Sample 1, except for using ethylbenzene (reagent grade, made by Tokyo Chemical Industry Co., Ltd.) in place of 3-ethyltoluene. The relative basicity of ethylbenzene was 0.02.

The measurement results of the relative basicities of the above Samples 1 to 10 are shown in the following Table 2. In Table 2, Samples are entered in the order from highest relative basicity.

TABLE 2

| Sample | | Relative Basicity[*] |
|---|---|---|
| Sample 7 | mesitylene | 5.00 |
| Sample 9 | 1,3,5-triethylbenzene | 3.52 |
| Sample 6 | pseudocumene | 1.63 |
| Sample 1 | 3-ethyltoluene | 0.52 |
| Sample 2 | 1-fluoronaphthalene | 0.37 |

TABLE 2-continued

| Sample | | Relative Basicity[*] |
|---|---|---|
| Sample 3 | fluoro-2,3,4,6-tetramethylbenzene | 0.29 |
| Sample 4 | metadiethylbenzene | 0.28 |
| Sample 5 | fluoro-2,4,6-trimethylbenzene | 0.16 |
| Sample 8 | OX | 0.04 |
| Sample 10 | ethylbenzene | 0.02 |

[*]the relative basicity of MX = 1

The mass amounts of the MX—HF—$BF_3$ complex and MX in each step described later were evaluated in such a way that the separated hydrogen fluoride solution phase and the oil phase were each withdrawn into ice water; the obtained hydrogen fluoride solution phase and oil phase were each subjected to a neutralization treatment to thereby obtain an oil fraction dissolved in the hydrogen fluoride solution and an oil fraction obtained by removing trace amounts of acid fractions from the oil phase, respectively; and thereafter, gas chromatography (GC-14B, made by SHIMADZU CORPORATION) was used and a calibration curve was fabricated using n-decane (reagent grade, made by Wako Pure Chemical Industries, Ltd.) as the internal standard substance. Here, a capillary column used was ULBON Xylene Master, made by SHINWA CHEMICAL INDUSTRIES LTD. (internal diameter: 0.32 mmϕ, length: 50 m). The temperature-rise program was such that the temperature was raised at a rate of 2° C./min from 70° C. to 150° C., and held for 30 min.

Example 1

[Acid-Base Extracting Step of MX]

As a raw material, a xylene mixture was used in which ethylbenzene, p-xylene, m-xylene and o-xylene (all were of reagent grade, made by Wako Pure Chemical Industries, Ltd.) were mixed so as to be contained, respectively, in 14%, 19%, 41% and 24% in terms of mass.

A rotary-disc extraction column (material: SUS316L-made) internally equipped with a total of 52 rotary discs and having an inner diameter of 45 mm and an entire length of 2,000 mm was held at an in-column temperature of 0° C. and at a nitrogen pressure of 0.4 MPa; the above xylene mixture was fed at a rate of 524 g/h from a feed pipe installed at a middle plate of the extraction column; and hexane (made by Godo Co., Ltd.) comprising 39 mol % of methylcyclopentane as a diluent was fed at a rate of 524 g/h from a pipe installed at a lower section of the extraction column. A mixed liquid comprising hydrogen fluoride, boron trifluoride, MX and metadiethylbenzene in a molar ratio of hydrogen fluoride:boron trifluoride:MX:metadiethylbenzene=5:0.5:0.04:0.56 was fed at a rate of 1738 g/h from a pipe installed at an upper plate of the extraction column; and extraction of MX was carried out. Here, in the system, a MX—HF—$BF_3$ complex and a metadiethylbenzene-HF—$BF_3$ complex were present as a mixture.

MX extracted with hydrogen fluoride and boron trifluoride was continuously discharged as a hydrogen fluoride solution of the MX—HF—$BF_3$ complex at a rate of 1370 g/h from a pipe installed at the column bottom of the extraction column. Further, the mixed components excluding the complex solution was continuously discharged at a rate of 1534 g/h from a pipe installed at the column top of the extraction column. The complex solution discharged from the column bottom contained the MX—HF—$BF_3$ complex and the metadiethylbenzene-HF—$BF_3$ complex, and their molar ratio was 60:8. The number of moles of the MX—HF—$BF_3$ complex in the discharged complex solution (hydrogen fluoride solution) was 0.995 with respect to the total number of moles of the xylene mixture in the complex solution. Further the MX extraction rate was calculated from the following expression, and was 92%.

MX extraction rate (%)=((the number of moles of [the MX—HF—$BF_3$ complex discharged from the extraction column]−the number of moles of [a MX—HF—$BF_3$ complex fed to the extraction column])/the number of moles of [MX in the fed xylene mixture])×100

[Complex Exchanging Step]

A rotary-disc extraction column (material: SUS316L) internally equipped with a total of 26 rotary discs and having an inner diameter of 45 mm and an entire length of 1,000 mm, as a complex exchange column, was held at an in-column temperature of 0° C. and at a nitrogen pressure of 0.4 MPa; the complex solution discharged in the above-mentioned MX extracting step was fed at a rate of 1367 g/h from a pipe installed at an upper plate of the extraction column. A mixed liquid comprising 20 mol % of hexane (made by Godo Co., Ltd.) comprising 39 mol % of methylcyclopentane as a diluent and 80 mol % of metadiethylbenzene as an eliminating agent was fed at a rate of 2422 g/h from a pipe installed at a lower section of the extraction column.

MX by which the eliminating agent was complex-exchanged in the complex exchange column was continuously discharged as a mixed liquid of the eliminating agent and the diluent at a rate of 1988 g/h from a pipe installed at the column top of the complex exchange column. The concentration of MX in the discharged mixed liquid and the concentration of metadiethylbenzene were, respectively, 11.2% and 55.2% in terms of mass. A hydrogen fluoride solution of a metadiethylbenzene-HF—$BF_3$ complex was continuously discharged at a rate of 1843 g/h from a pipe installed at the column bottom of the complex exchange column. The discharged complex hydrogen fluoride solution contained the MX—HF—$BF_3$ complex and the metadiethylbenzene-HF—$BF_3$ complex, and the proportion thereof was 8:112 in molar ratio. The MX complex exchange rate was calculated from the following expression, and was 88%.

MX complex exchange rate (%)=100−(the number of moles of [the MX—HF—$BF_3$ complex discharged from the complex exchange column])/(the number of moles of [the MX—HF—$BF_3$ complex fed to the complex exchange column])×100

From the above results, the MX yield when MX was separated from the xylene mixture being a raw material through the MX acid-base extracting step and the complex exchanging step was 81%. Here, the MX yield was calculated from the following expression.

MX yield (%)=the MX extraction rate (%)×the MX complex exchange rate (%)/100

Although conventional technologies needed to cool the column temperature to 0° C. or less in the complex formation time, and to heat it to 100° C. or more in the complex decomposition time, it is clear that since the method for separating alkyl aromatic hydrocarbons according to the present embodiment works only with cooling in the complex formation time, and can save the energy cost, the method is industrially advantageous.

[Isolation of MX]

In the above-mentioned complex exchanging step, the mixed liquid comprising MX discharged from the pipe installed at the column top of the extraction column was distilled to thereby isolate MX. First, about 1 kg of the MX mixed liquid comprising the eliminating agent and the diluent was distilled at a column top pressure of 93 kPa to be thereby separated into a component comprising mainly hexane and methylcyclopentane and having a boiling point less than MX, and a component having a boiling point equal to or more than MX. Then, the latter component was distilled at a column top pressure of 31 kPa to be thereby separated into a component comprising mainly MX and a component comprising mainly diethylbenzene, which has a higher boiling point than MX. About 105 g of MX was recovered by this two-stage distilling operation. The purity of MX was 99.8%. Here, the number of theoretical plates of the distillation column used was about 20 plates; the reflux ratio in each distilling operation was 30; and the distillation recovery rate of MX was 81%.

Example 2

The above operation was carried out as in Example 1, except for using 3-ethyltoluene in place of metadiethylbenzene as an eliminating agent. As a result, the MX extraction rate in the MX extracting step was 90%; the MX complex exchange rate in the complex exchanging step was 98%; and the MX yield when MX had been separated from the xylene mixture being a raw material through the MX extracting step and the complex exchanging step was 88%.

Example 3

The above operation was carried out as in Example 1, except for using pseudocumene in place of metadiethylbenzene as an eliminating agent. As a result, the MX extraction rate in the MX extracting step was 74%; the MX complex exchange rate in the complex exchanging step was 100%; and the MX yield when MX had been separated from the xylene mixture being a raw material through the MX extracting step and the complex exchanging step was 74%.

Example 4

The above operation was carried out as in Example 1, except for using fluoro-2,4,6-trimethylbenzene in place of metadiethylbenzene as an eliminating agent. The MX extraction rate in the MX extracting step was 93%; the MX complex exchange rate in the complex exchanging step was 70%; and the MX yield when MX had been separated from the xylene mixture being a raw material through the MX extracting step and the complex exchanging step was 65%.

Example 5

The above operation was carried out as in Example 1, except for using mesitylene in place of metadiethylbenzene as an eliminating agent. The MX extraction rate in the MX extracting step was 53%; the MX complex exchange rate in the complex exchanging step was 100%; and the MX yield when MX had been separated from the xylene mixture being a raw material through the MX extracting step and the complex exchanging step was 53%.

Comparative Example 1

The above operation was carried out as in Example 1, except for using o-xylene (OX) in place of metadiethylbenzene as an eliminating agent. The MX extraction rate in the MX extracting step was 71%; the MX complex exchange rate in the complex exchanging step was 1.6%; and the MX yield when MX had been separated from the xylene mixture being a raw material through the MX extracting step and the complex exchanging step was 1%.

In the separation of MX in Examples 1 to 5 and Comparative Example 1 described above, the MX extraction rate in the acid-base extracting step, the content proportion of the MX complex in the complex solution discharged from the column bottom of the extraction column (=the number of moles of the MX—HF—BF$_3$ complex with respect to the total number of moles of aromatic hydrocarbons having 8 carbon atoms (ethylbenzene, p-xylene, MX and o-xylene) in the discharged hydrogen fluoride solution, that is, the molar ratio of (the MX component in the hydrogen fluoride solution)/(the whole C8 aromatic hydrocarbons therein)), and the MX complex exchange rates in the complex exchanging step were, respectively, as shown in the following Table 3. In Table 3, Examples and Comparative Example were mentioned in the order of relative basicity of the eliminating agents used.

Comparative Example 2

[Acid-Base Extracting Step of MX]

A rotary-disc extraction column (material: SUS316L-made) internally equipped with a total of 52 rotary discs and having an inner diameter of 45 mm and an entire length of 2,000 mm was held at an in-column temperature of 0° C. and at a nitrogen pressure of 0.4 MPa; and hexane (made by Godo Co., Ltd.) comprising 39 mol % of methylcyclopentane as a diluent was fed at a rate of 524 g/h from a pipe installed at a lower section of the extraction column. A mixed liquid comprising hydrogen fluoride, boron trifluoride, ethylbenzene, p-xylene, MX and o-xylene in a molar ratio of hydrogen fluoride:boron trifluoride:MX:metadiethylbenzene=5:0.5:0.14:0.18:0.40:0.23 was fed at a rate of 1909 g/h from a pipe installed at an upper plate of the extraction column; and extraction of MX was carried out.

MX extracted with hydrogen fluoride and boron trifluoride was continuously discharged as a hydrogen fluoride solution of a MX—HF—BF$_3$ complex at a rate of 1429 g/h from a pipe installed at the column bottom of the extraction column. Further, mixed components excluding the complex solution was continuously discharged at a rate of 1005 g/h from a pipe installed at the column top of the extraction column. The molar ratio of MX, HF and BF$_3$ in the complex solution discharged from the column bottom was 0.39:5:0.5. The number of moles of the MX—HF—BF$_3$ complex in the discharged complex solution (hydrogen fluoride solution) was 0.995 with respect to the total number of moles of the xylene mixture in the complex solution. Further the MX extraction rate was calculated from the following expression, and was 98.5%.

MX extraction rate (%)=(the number of moles of [MX in the complex solution discharged from the column bottom of the extraction column])/(the number of moles of [MX in the mixed liquid fed])×100

[Complex Decomposing Step]

The MX—HF—BF$_3$ complex hydrogen fluoride solution obtained in the above was fed at a rate of 10 g/min to a complex decomposition column (SUS316L-made, inner diameter: 760 mm, length: 1760 mm, packed with Teflon Raschig rings of 1/2 inch) at a pressure of 0.4 MPa, at a column bottom temperature of 120° C. and under refluxing, to which column hexane was fed at a rate of 10 g/min; and hydrogen fluoride and boron trifluoride were recovered from the column top, and a hexane solution comprising MX was discharged from the column bottom section. The obtained hexane solution was subjected to a neutralization treatment to thereby obtain an oil layer. The MX complex decomposition rate and the MX recovery rate were calculated from the reaction result by gas chromatography, and were, respectively, 99.9% and 99.9%. Here, the complex decomposition rate and the MX recovery rate were calculated by the following expression. From the above result, the MX yield when MX had been separated from the xylene mixture being a raw material through the MX acid-base extracting step and the complex decomposing step was 98.41.

MX complex decomposition rate (%)=100−(the number of moles of boron trifluoride in the hexane solution/the number of moles of MX in the hexane solution)×100

MX recovery rate (%)=(the number of moles of MX in the hexane solution)/(the number of moles of the MX—HF—BF$_3$ complex fed)×100

[Isolation of MX]

By using the hexane solution containing MX discharged from the column bottom of the decomposition column in the complex decomposing step, MX was isolated by the same operation in Example 1. The purity of the obtained MX was 99.71, and the distillation recovery rate of the MX was 78%. It is clear that in the case of using the complex decomposition column, for the decomposition without deterioration of the complex, the column bottom temperature needs to be a temperature of 100° C. or more, and some heat quantity, which is unnecessary in Examples 1 to 5, is necessary.

was 0.995 with respect to the total number of moles of the xylene mixture in the complex solution, and the MX extraction rate was 92%, which exhibited the same result as in the preparation in the above-mentioned proportion.

Example 7

[Acid-Base Extracting Step of Mesitylene]

As a raw material, a C9 alkylbenzene mixture (made by Godo Co., Ltd.) was used which contained 7% of propylbenzenes, 36% of ethyltoluenes, 11% of mesitylene, 35% of pseudocumene, 6% of hemimellitene, 1% of indan, and 4% of the others.

A rotary-disc extraction column (material: SUS316L-made) internally equipped with a total of 52 rotary discs and having an inner diameter of 45 mm and an entire length of 2,000 mm was held at an in-column temperature of 0° C. and at a nitrogen pressure of 0.4 MPa; and the C9 alkylbenzene mixture was fed at a rate of 2392 g/h from a feed pipe installed at a middle plate of the extraction column, and hexane (made by Godo Co., Ltd.) containing 39 moll of methylcyclopentane as a diluent was fed at a rate of 524 g/h from a pipe installed at a lower section of the extraction column. A hydrogen fluoride solution (hydrogen fluoride: boron trifluoride:mesitylene:1,2,3-triethylbenzene=5:0.5: 0.002:0.66 in molar ratio) of a mesitylene-HF—BF$_3$ complex and a 1,2,3-triethylbenzene-HF—BF$_3$ complex was fed at a rate of 1676 g/h from a pipe installed at an upper plate of the extraction column; and extraction of mesitylene was carried out.

Mesitylene extracted with hydrogen fluoride and boron trifluoride was continuously discharged as a hydrogen fluo-

TABLE 3

| | Eliminating Agent | | MX Acid-Base Extracting Step | | | Complex Exchanging Step | | Complex Decomposing Step | | |
|---|---|---|---|---|---|---|---|---|---|---|
| | | | Extraction | MX | | Complex Exchange | MX Complex | Column Bottom | MX | Yield of MX |
| | Name | Relative Basicity[a] | Temperature (° C.) | Extraction Rate (%) | MX/C8 (mol/mol) | Temperature (° C.) | Exchange Rate (%) | Temperature (° C.) | Recovery Rate (%) | (%) |
| Example 5 | mesitylene | 5.00 | 0 | 53 | 0.995 | 0 | 100 | —[b] | | 53 |
| Example 3 | pseudocumene | 1.63 | | 74 | 0.995 | | 100 | | | 74 |
| Example 2 | 3-ethyltoluene | 0.52 | | 90 | 0.995 | | 98 | | | 88 |
| Example 1 | metadiethylbenzene | 0.28 | | 92 | 0.995 | | 88 | | | 81 |
| Example 4 | fluoro-2,4,6-trimethylbenzene | 0.16 | | 93 | 0.995 | | 70 | | | 65 |
| Comparative Example 1 | OX | 0.04 | | 71 | 0.990 | | 1.6 | | | 1 |
| Comparative Example 2 | — | — | 0 | 98.5 | 0.995 | — | — | 120 | 99.9 | 98.4 |

Remarks

[a]relative basicity, MX = 1

[b]Examples 1 to 5 need not the complex decomposing step needing a much heat quantity and can largely reduce the energy necessary for the decomposition.

Example 6

[Acid-Base Extracting Step of MX by Recycling an Eliminating Agent Complex]

The same operation as in the acid-base extracting step of MX in Example 1 was carried out, except for using the metadiethylbenzene-HF—BF3 complex discharged from the column bottom in the complex exchanging step in Example 1 as a mixed liquid fed from a pipe installed at an upper plate of the extraction column.

The number of moles of the MX—HF—BF3 complex in the complex solution discharged from the column bottom ride solution of a mesitylene-HF—BF$_3$ complex at a rate of 1460 g/h from a pipe installed at the column bottom of the extraction column. Further, mixed components excluding the complex solution was continuously discharged at a rate of 3132 g/h from a pipe installed at the column top of the extraction column. The complex solution discharged from the column bottom was a hydrogen fluoride solution (the molar ratio of the mesitylene-HF—BF$_3$ complex and the 1,2,3-triethylbenzene-HF—BF$_3$ complex was 9:55) of the mesitylene-HF—BF$_3$ complex and the 1,2,3-triethylbenzene-HF—BF$_3$ complex. The number of moles of the mesitylene-HF—BF$_3$ complex in the discharged complex solution (hydrogen fluoride solution) was 0.90 with respect to the total number of moles of the C9 alkylbenzene mixture charged. Further the mesitylene extraction rate was calculated from the following expression, and was 87%.

Mesitylene extraction rate (%)=((the number of moles of [the mesitylene-HF—$BF_3$ complex discharged from the extraction column]−the number of moles of [the mesitylene-HF—$BF_3$ complex fed to the extraction column])/the number of moles of [mesitylene in the C9 alkylbenzene mixture fed])×100

[Complex Exchanging Step]

A rotary-disc extraction column (material: SUS316L) internally equipped with a total of 26 rotary discs and having an inner diameter of 45 mm and an entire length of 1,000 mm, as a complex exchange column, was held at an in-column temperature of 0° C. and at a nitrogen pressure of 0.4 MPa; the complex solution discharged in the above-mentioned mesitylene extracting step was fed at a rate of 1300 g/h from a pipe installed at an upper plate of the extraction column. A mixed liquid containing 20 mol % of hexane (made by Godo Co., Ltd.) containing 39 mol % of methylcyclopentane as a diluent and 80 mol % of 1,2,3-triethylbenzene as an eliminating agent was fed at a rate of 2169 g/h from a pipe installed at a lower section of the extraction column.

Mesitylene by which the eliminating agent was complex-exchanged in the extraction column was continuously discharged as a mixed liquid of the eliminating agent and the diluent at a rate of 1299 g/h from a pipe installed at the column top of the extraction column. The concentration of mesitylene in the discharged mixed liquid and the concentration of 1,2,3-triethylbenzene therein were, respectively, 15.0% and 48.0% in terms of mass. A hydrogen fluoride solution of the 1,2,3-triethylbenzene-HF—$BF_3$ complex was continuously discharged at a rate of 2170 g/h from a pipe installed at the column bottom of the extraction column. The discharged complex hydrogen fluoride solution contained the mesitylene-HF—$BF_3$ complex and the 1,2,3-triethylbenzene-HF—$BF_3$ complex, and the proportion thereof was 0.26:99.74 in molar ratio. The mesitylene complex exchange rate was calculated from the following expression, and was 99.5%.

Mesitylene complex exchange rate (%)=100−(the number of moles of [the mesitylene-HF—$BF_3$ complex discharged from the complex exchange column])/(the number of moles of [the mesitylene-HF—$BF_3$ complex fed to the complex exchange column])×100

[Isolation of Mesitylene]

In the above-mentioned complex exchanging step, the mixed liquid containing mesitylene discharged from the pipe installed at the column top of the extraction column was distilled to thereby isolate mesitylene. First, 150 kg of mesitylene containing the eliminating agent and the diluent was distilled at a column top pressure of 93 kPa to be thereby separated into a component containing mainly hexane and methylcyclopentane and having a boiling point less than mesitylene, and a component having a boiling point equal to or more than mesitylene. Then, the latter component was distilled at a column top pressure of 31 kPa to be thereby separated into a component containing mainly mesitylene and a component containing mainly 1,2,3-triethylbenzene, which has a higher boiling point than mesitylene. 19.2 kg of mesitylene was recovered by this two-stage distilling operation. The purity of mesitylene was 99.5%. Here, the number of theoretical plates of a distillation column used was 85 plates; the reflux ratio in each distilling operation was 15; and the distillation recovery rate of mesitylene was 85%.

The present application is based on Japanese Patent Application (Japanese Patent Application No. 2012-147540), filed to the Japan Patent Office on Jun. 29, 2012, the entire contents of which are incorporated hereby by reference.

INDUSTRIAL APPLICABILITY

The separating method and the separating apparatus according to the present invention can largely reduce the energy necessary for separation of a high-purity alkyl aromatic hydrocarbon, as compared with conventional ones, and can be utilized as an industrially advantageous process.

REFERENCE SIGNS LIST

1 COMPLEX EXCHANGE COLUMN
2-1 DILUENT FEED PIPE
2-2 ELIMINATING AGENT FEED PIPE
3 ALKYL AROMATIC HYDROCARBON-SUPERACID COMPLEX FEED PIPE
4, 11 COLUMN TOP
5, 10 COLUMN BOTTOM
6 ACID-BASE EXTRACTION COLUMN
7 RAW MATERIAL MIXTURE FEED PIPE
8 ELIMINATING AGENT-SUPERACID COMPLEX FEED PIPE
9 DILUENT FEED PIPE

The invention claimed is:

1. An apparatus for separating an alkyl aromatic hydrocarbon comprising: an acid-base extraction column; and a complex exchange column,
wherein the acid-base extraction column comprises: a pipe for feeding a mixture comprising an alkyl aromatic hydrocarbon and one or more isomers thereof; a pipe for feeding a first diluent; a pipe for feeding a complex solution of an eliminating agent and a superacid withdrawn from a column bottom of the complex exchange column; a pipe for discharging the alkyl aromatic hydrocarbon as a complex solution of the alkyl aromatic hydrocarbon and the superacid from a column bottom of the acid-base extraction column; and a pipe for discharging a mixed liquid comprising the eliminating agent separated by the complex exchange, unextracted extraction residual isomers, and the diluent from a column top of the acid-base extraction column, and
wherein the complex exchange column comprises: a pipe for feeding the complex solution of the alkyl aromatic hydrocarbon and the superacid discharged from the column bottom of the acid-base extraction column; a pipe for feeding a second diluent and the eliminating agent; a pipe for discharging a mixed liquid comprising the extracted alkyl aromatic hydrocarbon, the eliminating agent and the diluent from a column top of the complex exchange column; and a pipe for discharging a complex solution of the eliminating agent and the superacid after the complex exchange has been carried out from the column bottom of the complex exchange column.

2. The apparatus according to claim 1, wherein the pipe for feeding the second diluent and the eliminating agent is separated into a pipe for feeding the second diluent and a pipe for feeding the eliminating agent.

3. The apparatus according to claim 1, wherein in the complex exchange column, the complex solution of the alkyl aromatic hydrocarbon and the superacid fed, and the fed mixed solution of the second diluent and the eliminating agent are brought into countercurrent contact.

4. The apparatus according to claim 1, further comprising a distillation column to distill the mixed liquid comprising the alkyl aromatic hydrocarbon, the eliminating agent and the diluent discharged from the complex exchange column to thereby separate the alkyl aromatic hydrocarbon, the eliminating agent and the diluent.

5. The apparatus according to claim 1, further comprising a distillation column to distill the mixed liquid comprising the eliminating agent, the unextracted extraction residual isomers and the diluent discharged from the acid-base extraction column to thereby separate the eliminating agent, the extraction residual isomers and the diluent.

* * * * *